(12) United States Patent
Ulbrich et al.

(10) Patent No.: US 11,439,814 B2
(45) Date of Patent: Sep. 13, 2022

(54) STIMULATION DEVICE FOR ELECTROTHERAPY AND METHOD FOR CHECKING THE POLARITY OF CONTACT ELECTRODES

(71) Applicant: GS ELEKTROMEDIZINISCHE GERÄTE G. STEMPLE GMBH, Kaufering (DE)

(72) Inventors: Mark Ulbrich, Kaufering (DE); Michael Peukert, Kaufering (DE)

(73) Assignee: GS Elektromedizinische Geräte G. Stemple GmbH, Kaufering (DE)

( * ) Notice: Subject to any disclaimer, the term of this patent is extended or adjusted under 35 U.S.C. 154(b) by 0 days.

(21) Appl. No.: 16/972,459

(22) PCT Filed: Feb. 5, 2020

(86) PCT No.: PCT/IB2020/050928
§ 371 (c)(1),
(2) Date: Dec. 4, 2020

(87) PCT Pub. No.: WO2020/183253
PCT Pub. Date: Sep. 17, 2020

(65) Prior Publication Data
US 2021/0393952 A1    Dec. 23, 2021

(30) Foreign Application Priority Data
Mar. 12, 2019   (DE) .................. 10 2019 106 224.1

(51) Int. Cl.
*A61N 1/08*   (2006.01)
*A61N 1/39*   (2006.01)
(Continued)

(52) U.S. Cl.
CPC ............. *A61N 1/08* (2013.01); *A61N 1/3625* (2013.01); *A61N 1/371* (2013.01); *A61N 1/3904* (2017.08);
(Continued)

(58) Field of Classification Search
CPC ........ A61N 1/08; A61N 1/3625; A61N 1/371; A61N 1/3904; A61N 1/3937
See application file for complete search history.

(56) References Cited

U.S. PATENT DOCUMENTS 8,738,130 B2    5/2014  Freeman et al.
11,154,230 B2*  10/2021 Sullivan ............... A61B 5/6805
(Continued)

FOREIGN PATENT DOCUMENTS

EP     0473861 A1 *  3/1992  ............... A61N 1/40
WO  WO-2017201560 A1 * 11/2017  ......... G01R 27/2605

OTHER PUBLICATIONS

International Search Report dated Apr. 17, 2020 for International Application No. PCT/IB2020/050928.

Primary Examiner — Catherine M Voorhees
(74) Attorney, Agent, or Firm — Fay Sharpe LLP

(57) ABSTRACT

The invention relates to a stimulation device for electrotherapy, in particular a defibrillator device and/or external pacemaker device, comprising at least two contact electrodes, which can be applied to the body of a patient at suitable stimulation positions and by means of which current pulses can be applied to the body of the patient, the first of the at least two contact electrodes acting as a charging electrode having positive polarity, and the second of the at least two contact electrodes acting as a discharging electrode having negative polarity with respect to an emitted current pulse, and with a current pulse generator, which is or can be connected to the contact electrodes by means of line connections. The invention further relates to a method for
(Continued)

determining the polarity of contact electrodes applied to the body of a patient.

9 Claims, 3 Drawing Sheets

(51) Int. Cl.
  *A61N 1/362* (2006.01)
  *A61N 1/37* (2006.01)
(52) U.S. Cl.
  CPC ...... *A61N 1/3937* (2013.01); *A61N 2001/083* (2013.01)

(56) References Cited

U.S. PATENT DOCUMENTS

| | | | |
|---|---|---|---|
| 2005/0267536 A1* | 12/2005 | Freeman | A61N 1/3918 607/5 |
| 2007/0100381 A1* | 5/2007 | Snyder | A61N 1/3937 607/5 |
| 2014/0236248 A1 | 8/2014 | Gilman et al. | |
| 2014/0277226 A1 | 9/2014 | Poore et al. | |
| 2017/0221384 A1* | 8/2017 | Peng | G09B 23/28 |

* cited by examiner

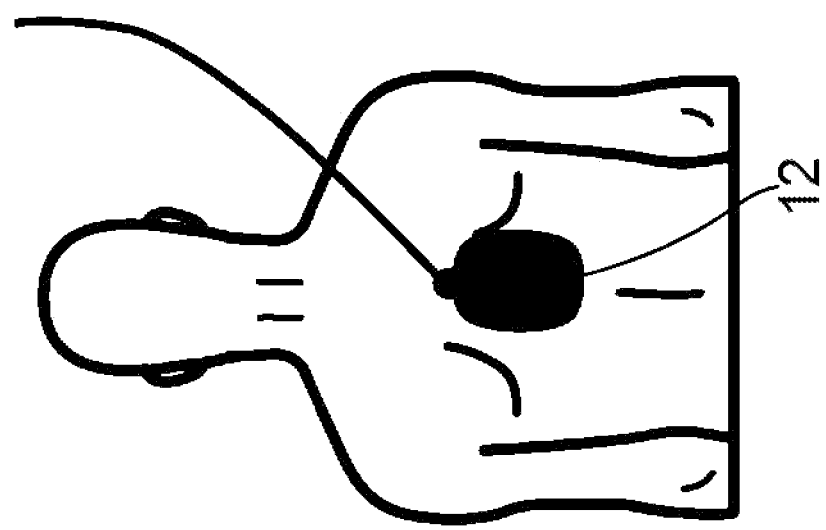
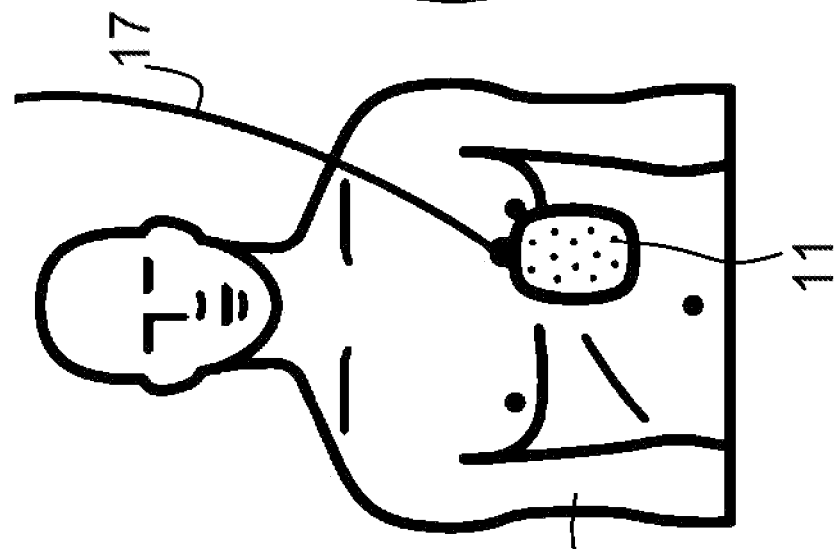
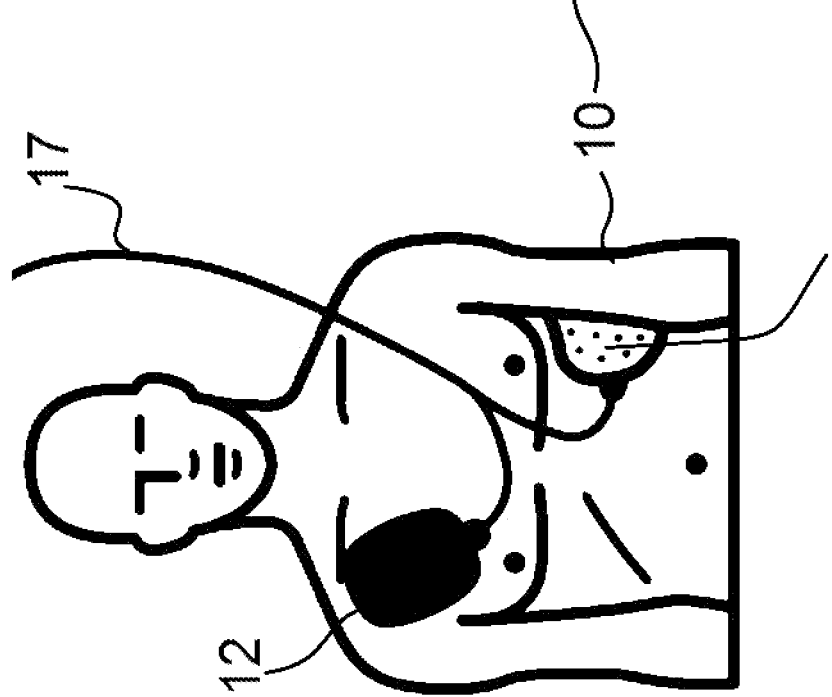
Fig.1A Fig.1B

STIMULATION DEVICE FOR ELECTROTHERAPY AND METHOD FOR CHECKING THE POLARITY OF CONTACT ELECTRODES

BACKGROUND

Stimulation devices suitable for use for defibrillation or as external pacemakers are generally connected to the body of the patient to be treated by means of two contact electrodes which are fixed, for example glued, to certain positions on the upper body of the patient. In doing so, the contact electrodes are basically identical, i.e. both electrodes can act both as a charging electrode and as a discharging electrode.

With respect to the emitted current pulse, the electrode with positive polarity thereby acts as the charging electrode and the electrode with negative polarity as the discharging electrode.

Standard electrode positions for external pacemakers (pacers) and defibrillators are thereby the positions "anterior-posterior" and "anterior-lateral". With the arrangement "anterior-lateral", the polarity of the electrode applied on the anterior, i.e. on the right side of the front upper chest, shall be positive, while the polarity of the electrode applied on the lateral, i.e. (left) placed laterally below the armpit is negative. With the arrangement "anterior-posterior", the electrode applied on the posterior, that is to say on the back of the patient, shall have positive polarity, while the electrode applied on the front, that is to say on the chest, shall have negative polarity. The polarity of the electrodes is decisive for a reasonable therapy, as a reversal of the polarity raises the coupling threshold considerably, which can challenge the success of the therapy. It is comprehensible that especially in emergency situations in which the rescuers can be under great temporal and also psychological pressure, it can easily happen unintentionally that the polarity on the electrodes to carry out a defibrillation or to establish a connection with an external—pacemaker is reversed, in which case the success of the treatment is impaired or completely challenged.

BRIEF DESCRIPTION

The object of the invention is to create a stimulation device of the type mentioned at the outset, with which the correct positioning of the contact electrodes on the body of the patient is simplified.

This object is achieved with the invention by means of a signal evaluation unit that is or can be connected to the contact electrodes for determining the application positions of the contact electrodes on the body of the patient. In doing so, according to the method according to the invention, it is made possible to check the polarity of contact electrodes of the stimulation device for electrotherapy applied to the body of a patient, in particular a defibrillator and/or pacemaker device, in that, by means of the contact electrodes applied to the body of the patient, body's own signals specific to the respective application location of the contact electrodes are recorded and transmitted to an evaluation unit, wherein the evaluation unit, based on the signals detected on the contact electrodes, e.g. their orientation and/or size, determines the actual position of the contact electrodes on the body of the patient. This can be displayed to the paramedic or doctor by means of a suitable display, in order to induce them to manually reverse the polarity of the contact electrodes. Accordingly, the device according to the invention can thus have a display device for displaying the application position of the charging electrode and the discharging electrode on the body of the patient.

It is particularly advantageous if the evaluation unit compares the polarity of the treatment current provided for the electrotherapy actually applied to the respective contact electrode with a target polarity on the contact electrode at the respective actual position and, if the actual polarity and the target polarity do not match, outputs a signal and/or changes the actual polarity to the target polarity. In this way, the paramedic or doctor is given not only the respective polarity of the contact electrodes applied to the body of the patient, but also, if necessary, that the polarity has been reversed or, in a particularly preferred, advantageous manner, the error is immediately corrected by the device according to the invention itself when the electrodes are connected. The rescue personnel can therefore rely on the fact that the patient will receive the optimal therapy even if the electrodes are incorrectly applied (reversed). This can save valuable time.

In order to carry out the method according to the invention, the device is preferably provided with switching means for reversing the line connections between the current pulse generator and the contact electrodes. The switching means make it superfluous to switch the cable connections connected between the contact electrodes and the defibrillator/external pacemaker, if an incorrect polarity of the contact electrodes has been determined by the device. The switching means can comprise a change-over switch, during whose operation the pole reversal takes place quickly. It is thereby particularly advantageous if the change-over switch can be actuated in a controlled manner by the evaluation unit so that the switchover can take place automatically without manual intervention by the operating personnel of the device.

The signals evaluated by the device can preferably be ECG signals that are picked up by the electrodes at the positions where the contact electrodes were placed on the body of the patient and are transmitted to the evaluation unit of the stimulation device via the line connections connected thereto. Since the ECG signals differ significantly depending on the location of the contact electrodes, the location of the two contact electrodes on the body of the patient can be deduced clearly from the extraction of features from the DE-ECG derivation. Other types of signals that can be evaluated in order to deduce the respective location of the positioning of the contact electrodes can e.g. be biopotentials or the impedance of the tissue at the location of the applied contact electrodes.

BRIEF DESCRIPTION OF THE DRAWINGS

Further advantages and features of the invention unfold from the following description and from the drawing, in which a preferred embodiment of the invention is explained in more detail by means of an example. It shows:

FIG. 1A a representation of the standard electrode position "anterior-lateral" for external pacemakers and defibrillators;

FIG. 1B a representation of the standard electrode positions "anterior-posterior";

DETAILED DESCRIPTION

FIG. 1 shows two standard electrode positions for the arrangement of contact electrodes 11, 12 on the body of a patient 10, such as are used for external pacemakers or defibrillators.

Figure 2A:
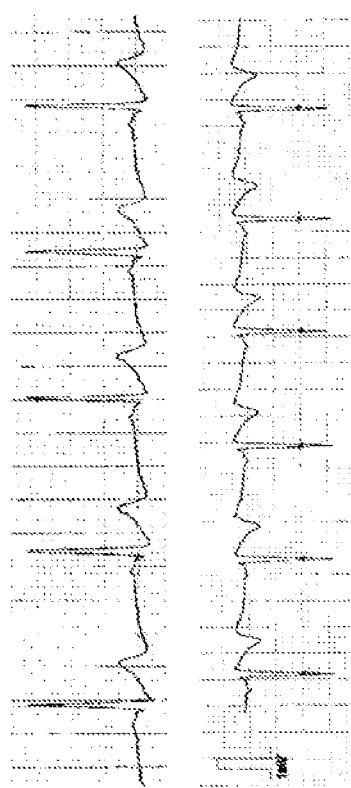
FIG. 2A ECG signals that can be obtained from the electrode position according to FIG. 1A with correct polarity (above) and reversed polarity (below)
Figure 2B:
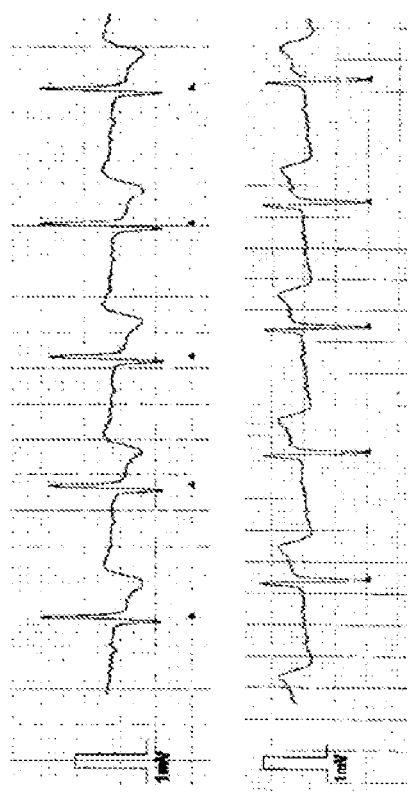
FIG. 2B ECG signals that can be obtained from the electrode position according to FIG. 1B with correct polarity (above) and reversed polarity (below)

When applying the electrodes to the patient, it is important not only to ensure that they are correctly positioned, but also that the correct polarity of the electrical pulses introduced into the body of the patient by the defibrillator or pacemaker via electrodes 11,12 is observed. In the two electrode positions shown in FIGS. 1A and 1B, the polarity of the dotted electrode 11 should be negative and the polarity of the electrode 12 shown as flat black should be positive. If the ECG signals recorded by the contact electrodes 11,12 at the points shown are derived and recorded, the ECG signal paths respectively shown above in FIGS. 2A and 2B are obtained, if the correct polarity is observed as explained above. When the polarity is reversed, the course of the ECG response signal also changes; it then appears as respectively depicted in FIGS. 2A and 2B below. It can be seen that by reversing the polarity, the characteristic features of the recorded waves change and on the basis of this it is easy to see whether the polarity of the two contact electrodes corresponds to the desired arrangement or has been reversed.

Figure 3:
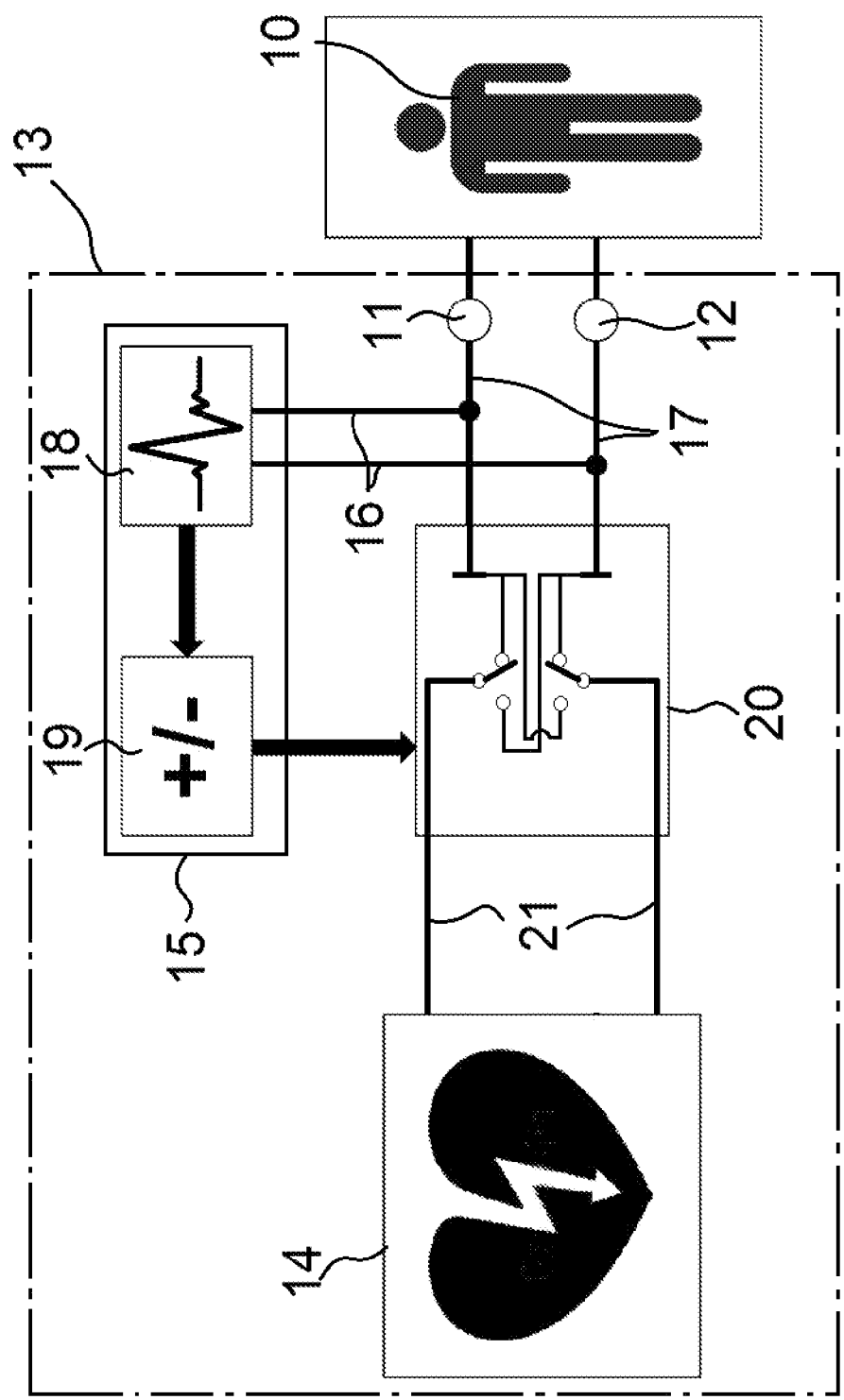
FIG. 3 a schematic representation of the stimulation device according to the invention for carrying out the method according to the invention.

The stimulation device shown schematically in FIG. 3, denoted in its entirety by 13, comprises, in addition to the two contact electrodes 11,12, a current pulse generator 14 and an ECG evaluation unit 15, which are connected with the contact electrodes 11,12 by means of conductor cables 16 and connection cables 17. The evaluation unit 15 has a display device 18 for the visual representation of the ECG signals picked up by the contact electrodes 11,12 as well as a signal processing device 19 with which it is determined on the basis of the recorded ECG signal, at which position on the body of the patient the charging electrode 12 with positive polarity and where the discharging electrode 11 with negative polarity is located.

If the evaluation unit 15 detects a reversal of the two contact electrodes in their target positions (FIG. 1) on the body of the patient 10, it will, by operating a double change-over switch 20, effect an exchange of the line connections 21 from the current pulse generator 14 to the connection cables 17 of the contact electrodes 11,12. In this way, the polarity of the treatment current for electrotherapy, provided by the current pulse generator 14, applied to the respective contact electrode is compared with a target polarity on the contact electrode at the respective actual position and, if the actual polarity and target polarity do not match, the actual polarity is changed to the target polarity. In the preferred exemplary embodiment, the polarity of the two contact electrodes is automatically reversed, so that the charge and discharge of the current respectively takes place at the correct point on the body of the patient 19, without it being necessary to disconnect the connection cables between the electrodes and the current pulse generator and to reconnect them after reversing the polarity.

The invention claimed is:

1. A stimulation device for electrotherapy, in particular defibrillator and/or an external pacemaker device, comprising:
   at least two contact electrodes, which can be applied to suitable stimulation positions on the body of a patient, and are configured to subject the body of the patient to current pulses, wherein the first of the at least two contact electrodes acts as a charging electrode having positive polarity and the second of the at least two contact electrodes acts as a discharging electrode having negative polarity with respect to an emitted current pulse;
   a current pulse generator, which is or can be connected to the contact electrodes via line connections; and
   a signal evaluation unit, which is or can be connected to the contact electrodes, wherein the stimulation device is arranged, through the contact electrodes applied to the body of the patient, to record endogenous signals from the patient specific to the respective stimulation positions of the contact electrodes and to transmit them to the evaluation unit, wherein the evaluation unit is configured to determine the actual stimulation positions of the contact electrodes on the body of the patient based on the specific signals detected by the contact electrodes.

2. The device according to claim 1, further comprising a display device configured to display the stimulation position of the charging electrode and the discharging electrode on the body of the patient.

3. The device according to claim 1, further comprising a switch configured to interchange the line connections between the current pulse generator and the contact electrodes.

4. The device according to claim 3, wherein the switch comprises a change-over switch.

5. The device according to claim 4, wherein the change-over switch can be actuated by the evaluation unit in a controlled manner.

6. The device according to one of claim 1, wherein the specific signals are ECG signals.

7. A method for checking the polarity of contact electrodes applied to the body of a patient of a stimulation device for electrotherapy, in particular a defibrillator device and/or pacemaker device, the method comprising: applying the contact electrodes to the body of the patient at suitable stimulation positions, recording endogenous signals from the patient specific to the respective stimulation positions of the contact electrodes, and transmitting the signals to an evaluation unit, wherein the evaluation unit determines an actual position of the contact electrodes on the body of the patient based on the signals detected at the contact electrodes.

8. The method according to claim 7, wherein the evaluation unit compares the polarity of the treatment current provided for the electrotherapy actually applied to the respective contact electrode with a target polarity at the contact electrode at the respective actual position and, when the actual polarity and the target polarity do not match, outputs a signal and/or changes the actual polarity to the target polarity.

9. The method according to claim 7, wherein the specific signals are ECG signals.

* * * * *